(12) United States Patent
Chowdhury

(10) Patent No.: US 10,953,210 B2
(45) Date of Patent: *Mar. 23, 2021

(54) MICRONEEDLE TRANSDERMAL DELIVERY DEVICE

(71) Applicant: Dewan Fazlul Hoque Chowdhury, Loughborough (GB)

(72) Inventor: Dewan Fazlul Hoque Chowdhury, Loughborough (GB)

( * ) Notice: Subject to any disclaimer, the term of this patent is extended or adjusted under 35 U.S.C. 154(b) by 566 days.

This patent is subject to a terminal disclaimer.

(21) Appl. No.: 15/595,669

(22) Filed: May 15, 2017

(65) Prior Publication Data

US 2017/0312488 A1    Nov. 2, 2017

Related U.S. Application Data

(63) Continuation of application No. 12/580,078, filed on Oct. 15, 2009, now Pat. No. 9,649,483, which is a continuation of application No. PCT/GB2008/000998, filed on Mar. 25, 2008.

(30) Foreign Application Priority Data

Apr. 16, 2007    (GB) ...................................... 0707282

(51) Int. Cl.
*A61M 37/00*    (2006.01)

(52) U.S. Cl.
CPC ... *A61M 37/0015* (2013.01); *A61M 2037/003* (2013.01); *A61M 2037/0061* (2013.01)

(58) Field of Classification Search
CPC .... A61M 2037/0023; A61M 2037/003; A61M 2037/0046; A61M 2037/0061; A61M 2037/0038; A61M 37/0015; A61M 5/3298; A61M 5/00; A61M 5/3295; A61M 5/32; A61M 5/178; A61M 5/3287; A61M 2005/3289; A61M 37/00; A61M 2210/04; A61B 17/205; A61B 5/150984; A61K 9/0021

See application file for complete search history.

(56) References Cited

U.S. PATENT DOCUMENTS

| | | | | | |
|---|---|---|---|---|---|
| 2,101,737 | A | * | 12/1937 | Gesler | B26B 21/34 30/30 |
| 2,247,440 | A | * | 7/1941 | Hempel | A61H 15/0085 601/147 |
| 2,330,853 | A | * | 10/1943 | Wintercorn | B26B 21/34 30/32 |
| 2,359,933 | A | * | 10/1944 | Niblack | A61H 15/0078 601/99 |
| 2,867,214 | A | * | 1/1959 | Wilson | A61B 17/54 606/131 |
| 3,276,121 | A | * | 10/1966 | Larson | B26B 21/34 30/346 |
| 3,521,322 | A | * | 7/1970 | Wenzel | A22C 25/08 452/177 |

(Continued)

*Primary Examiner* — Scott J Medway
(74) *Attorney, Agent, or Firm* — McCracken & Gillen LLC

(57) ABSTRACT

A drug delivery device that delivers pharmacologically active substances transdermally using microneedles arranged on a belt mounted rotatably about a plurality of rollers, the microneedles having an associated drug reservoir mounted on the belt which is compressed when the needles and belt are brought into contact with the skin.

12 Claims, 9 Drawing Sheets

(56) References Cited

U.S. PATENT DOCUMENTS

| | | | | |
|---|---|---|---|---|
| 3,762,045 A * | 10/1973 | Fitzpatrick, Jr. | B26B 21/26 | 30/40.1 |
| 3,918,449 A * | 11/1975 | Pistor | A61M 37/00 | 604/47 |
| 4,039,109 A * | 8/1977 | Rhodes | B65H 51/14 | 226/172 |
| 4,083,327 A * | 4/1978 | Dowdy | A01K 13/002 | 119/601 |
| 4,483,348 A * | 11/1984 | Sher | A61B 17/34 | 600/556 |
| 4,729,147 A * | 3/1988 | Armbruster | A47L 5/36 | 15/314 |
| 5,139,029 A * | 8/1992 | Fishman | A61B 5/411 | 600/556 |
| 5,190,558 A * | 3/1993 | Ito | A61B 17/322 | 604/289 |
| 5,207,183 A * | 5/1993 | Praschnik | A01K 13/002 | 119/609 |
| 5,964,729 A * | 10/1999 | Choi | A61B 17/205 | 604/47 |
| 6,050,988 A * | 4/2000 | Zuck | A61B 5/14514 | 604/890.1 |
| 6,083,196 A * | 7/2000 | Trautman | A61B 5/14514 | 604/46 |
| 6,193,679 B1 * | 2/2001 | Quinn | A61H 7/002 | 601/136 |
| 6,589,202 B1 * | 7/2003 | Powell | A61B 10/0045 | 604/27 |
| 6,611,707 B1 * | 8/2003 | Prausnitz | A61B 5/14514 | 604/21 |
| 7,727,147 B1 * | 6/2010 | Osorio | A61M 5/14244 | 600/365 |
| 7,909,776 B2 * | 3/2011 | Roe | A61B 5/15184 | 600/583 |
| 8,216,264 B2 * | 7/2012 | Konya | A61B 5/150022 | 606/182 |
| 8,376,984 B2 * | 2/2013 | James | A61M 37/0015 | 604/46 |
| 8,882,717 B2 * | 11/2014 | Kimmell | A61M 5/14593 | 604/173 |
| 9,138,179 B2 * | 9/2015 | Hoenes | A61B 5/150358 | |
| 9,301,588 B2 * | 4/2016 | Eckhouse | A61B 18/14 | |
| 9,649,483 B2 * | 5/2017 | Chowdhury | A61M 37/0015 | |
| 10,004,887 B2 * | 6/2018 | Gross | A61M 37/0015 | |
| 10,485,217 B2 * | 11/2019 | Baier | A46B 3/18 | |
| 2003/0083645 A1 * | 5/2003 | Angel | A61M 5/14248 | 604/890.1 |
| 2003/0211619 A1 * | 11/2003 | Olson | A61B 5/150358 | 436/44 |
| 2004/0087992 A1 * | 5/2004 | Gartstein | A61B 17/205 | 606/186 |
| 2005/0277849 A1 * | 12/2005 | Wong | A61B 5/1519 | 600/583 |
| 2006/0206062 A1 * | 9/2006 | Naimark | A61M 25/0069 | 604/264 |
| 2007/0088264 A1 * | 4/2007 | Liebl | A61M 37/00 | 604/117 |
| 2007/0161964 A1 * | 7/2007 | Yuzhakov | A61M 37/0015 | 604/272 |
| 2007/0288078 A1 * | 12/2007 | Livneh | A61B 18/1477 | 607/147 |
| 2009/0043247 A1 * | 2/2009 | Kreindel | A61B 18/14 | 604/21 |
| 2010/0216607 A1 * | 8/2010 | Mueller | A63B 22/0207 | 482/54 |
| 2010/0256594 A1 * | 10/2010 | Kimmell | A61M 37/0015 | 604/506 |
| 2012/0004638 A1 * | 1/2012 | Zimmerman | A61M 37/0015 | 604/506 |
| 2015/0059800 A1 * | 3/2015 | Shinoda | A45D 44/005 | 132/320 |
| 2016/0242689 A1 * | 8/2016 | Roehr | A61B 5/150389 | |

\* cited by examiner

MICRONEEDLE TRANSDERMAL DELIVERY DEVICE

CROSS-REFERENCE TO RELATED PATENT APPLICATIONS

The present patent application is a continuation of U.S. non-provisional patent application Ser. No. 12/580,078, filed Oct. 15, 2009, entitled "Microneedle Transdermal Delivery Device" which is a continuation of PCT/GB2008/000998 filed Mar. 25, 2008, designating the United States, which claims the benefit of Great Britain Application No. 0707282.0 filed Apr. 16, 2007, the entire teachings and disclosures of which are incorporated herein, in their entireties, by reference thereto.

FIELD OF THE INVENTION

The invention relates generally to drug delivery, and specifically relates to devices that deliver pharmacologically active substances transdermally using microneedles. The invention also relates to transdermal retrieval of body fluid for analysis.

BACKGROUND OF THE INVENTION

Microneedles are a recent invention arising from the application of etching and lithographic techniques from the semiconductor fabrication processes, to produce sharp, high aspect ratio, solid or hollow features on materials such as plastics or metals, which are termed "microneedles" because they have dimensions on the micrometre scale.

Microneedles have strong potential for the transdermal delivery of a very wide range of drugs, pharmacologically active agents and therapeutic agents, for both immediate effect and possibly for sustained action through appropriate formulation enhancements, and indeed have found potential applications as a mechanism for the delivery of drugs and various therapeutic molecules. The range of molecules in terms of size, chemistry or the dosage formulation in which the agent is contained that may be administered into humans and animals using microneedles is virtually unlimited.

There are a number of advantages associated with the use of microneedles for the delivery of drugs through the skin, i.e. transdermally. The first of these relates to the advantages relating to the mechanism of drug absorption and distribution when administered through the skin, such as avoidance of the first pass metabolism by the liver, and a reduction of side effects, together with the rapid onset of action. Additionally in this case there are a number of further advantages ranging from the ability to deliver drugs of almost any physicochemical nature, any type of formulation, e.g., liquid, gel, emulsion, or even as a solid whereby the drug could form part of the needle or be used to coat the needle.

Microneedles are generally fabricated in arrays, synthesised using etching techniques, such as chemical or physical etching and standard lithographic procedures. The materials used range from silicon to polymers such as PDMS. They generally measure tens of microns to hundreds of microns in length and have varying tip diameters, usually less than 10 microns.

Some examples of microneedles are shown in FIG. 16.

It has been demonstrated ("Microfabricated microneedles: a novel approach to transdermal drug delivery" J Pharm Sci. 1998 August; 87(8):922-5") that application of microneedles on the human skin for 10 seconds resulted in a 1000-fold increase in permeability of the skin to calcein. However upon removal of the microneedle array there was a 10,000-fold increase in permeation. i.e., drug was able to permeate much more readily through the holes/microchannels created by the microneedles.

It has also been demonstrated ("Transdermal delivery of desmopressin using a coated microneedle array patch system". J Control Release. 2004 Jul. 7; 97(3):503-11) that an array of solid microneedles coated with the drug desmopressin was able to deliver more than 90% of the drug transdermally, with metabolites comparable to those produced when desmopressin is delivered intravenously.

The delivery of vaccines requires a strong immune response to optimise the effect of the drug, and such response is generally achieved through the use of adjuvants designed to boost the immune response. The skin is a major immunological organ with antigen-presenting Langerhans cells in rich supply, covering almost 15% of the surface area of the skin. Vaccines delivered by the transdermal route are taken up by these Langerhans cells and migrate to the lymph nodes where antigen-specific immunity is activated. This provides a highly efficient means therefore for administering vaccines.

Skin Penetration

The mechanics of microneedle insertion into the skin are critical to its practical application. Needles with the correct geometry and physical properties, such as strength, are able to penetrate the skin provided the penetration force is less than the breaking force of the needle/tip. The optimum needle types are those with a small tip radius and high wall thickness.

Another factor for drug delivery is ensuring that microneedles penetrate to the correct depth. Penetration depth is partly dictated by needle shape, and partly by needle diameter, inter-needle spacing, length and applied force.

In addition to the design and geometry of the needles due consideration must be given to the method by which the microneedles are applied to the skin, to ensure the requisite depth of penetration occurs, and such that drug permeation is predictable and not erratic.

There are a number of organizations developing microneedle based systems for the drug delivery applications, and each is developing and optimising the needles for its particular application. Generally speaking these systems are split between using solid microneedles to simply create cavities through which drug will then permeate, and using hollow microneedles, the bore of which acts as a conduit for the transport of drug from a reservoir upon compression of the drug reservoir, usually by hand.

The mechanism by which microneedles are adhered or applied to the skin is therefore very important and a number of different techniques are illustrated in the literature. The most common method is depression of an array of microneedles on the skin and holding for a defined period of time. For example, it is known from International Patent Application WO 2006/055771 to propel a microneedle array to the skin surface from a predetermined distance, whereas International Patent Application WO 2006/055795 teaches that a flexible sheet can be used to move a microneedle array in the direction of the skin surface.

An alternative propulsion means is known from International Patent Application WO 2006/055802, which uses an elastic band to propel a microneedle array towards the skin. Finally, International Patent Application WO 2007/002521 teaches an impactor which accelerates a microneedle array towards the surface of the skin, moving along an arcuate path.

Another known device is the 'Dermaroller™', which is used for both cosmetic and drug delivery applications. This uses a cylinder with surface projections of solid stainless steel microneedles of varying geometries. Cavities are created in the skin using the solid array of microneedles. Drug delivery is achieved by using the roller to 'press' drug or cosmetic material stored on a needle-free area of the roller in to the cavities created. An example of the roller is shown in FIG. 17.

A number of mechanisms have been developed to address the need for a reproducible means of applying the microneedles to the skin, which is crucial to their clinical exploitation. The majority of methods rely on the impact of an array of needles with the skin, either through mechanical means or manually by depressing with the thumbs for example.

The Dermaroller is one example whereby the force is applied using a cylinder to simultaneously bring the needles into contact with the skin and apply pressure over the region where the needles are in contact with the skin, followed by a region where the outer surface of the cylinder is absent of needles and is coated with drug which are claimed to be manually compressed and forced into the cavities created by the microneedles. There are two problems with the Dermaroller. First, the surface area of the skin through which drug permeation will occur cannot be easily determined as there is no mechanism for limiting the area over which the Dermaroller is applied. Secondly, the technique is inherently unreliable in accurately delivering a defined quantity because it depends entirely upon drug entering the skin through a combination of diffusion and forced entry by compression through the cavities created by the needles. In a clinical setting it is very important to be able to accurately define how much drug is administered.

The other known microneedle devices do not provide a satisfactory means of supplying accurate quantities of drugs transdermally in a controllable fashion, nor any means for staged delivery.

Embodiments of the invention overcome the problems with the Dermaroller and improve on the known devices.

BRIEF SUMMARY OF THE INVENTION

Embodiments of the invention generally provide a microneedle time-controlled patch and applicator device which can pump a defined amount of a substance through the bore of a hollow microneedle or microneedles into the skin at a predetermined depth.

The device ensures that the microneedles penetrate the skin in the desired manner and to the desired depth in a reproducible manner. It may have an integral pumping means for forcing the substance through the bore of the microneedle into the depth of the skin from where it will diffuse into the systemic circulation.

The substance could be any of various substances including drugs, pharmacologically active agents or therapeutic agents. Where any of these words is used, it will be understood to include the others.

The microneedle device is suitable for use with drugs of almost any type of formulation, which could range from liquid to solid. When the device is used in a timed controlled delivery mode or version, it is particularly well suited to delivering drugs with a short half life such as sumatriptan succinate.

The microneedle time-controlled patch and applicator will preferably provide a means of inserting the needles into the skin without using high impact forces, and furthermore it may simultaneously or nearly simultaneously pump defined quantities of drug through the bores of the microneedles to defined depths within the skin. Furthermore the device will ensure there is good contact between the needles and the skin at the point of administration to prevent backflow of drug by actively forcing the drug through the bores of the microneedles into the skin. The device will preferably force the drug into the skin without allowing any liquid to travel back up the bores into the drug reservoir, without the use of external pistons or pumps.

The mechanism may be incorporated into a patch for the time-controlled delivery of drugs from the microneedles, with appropriate microelectronic circuitry, or may be operated manually for a bolus dose or for vaccine delivery.

The invention has one or more suitable microneedles with a bore therethrough. The bore may be a bore running centrally through the microneedle with an exit at or near the tip. The microneedles extend away from a substrate, and may be arranged thereon in regular arrays such as single rows. The orientation and geometry of the microneedles relative to the substrate will be such that their penetration through the skin will be enhanced during travel over an arcuate pathway. As shown in the drawings, the rows may extend substantially perpendicularly to the direction of movement of the microneedles. As shown in FIGS. 3, 6 and 7, the microneedles may have a generally triangular profile and be arranged so that a sharp leading edge is directed towards the skin for entry into it. The bore may exit through the leading edge near the tip. The microneedles may be made from any suitable materials, ranging from silicon and stainless steel to plastics.

Each microneedle substrate may be mounted about a single roller. In a preferred alternative embodiment, each substrate is provided on a belt or track that runs around one or more rollers to form a conveyor mechanism. Preferably the belt forms a closed loop about the rollers but it could alternatively be unwound from a first roller and wound onto a last roller. It will be understood that the terms "belt", "track" and "loop" are used generally interchangeably in this description.

The rollers may be slidably and rotatably mounted about their axes on a guide on a frame, so that the loop can rotate around the rollers, and the rollers and loop can simultaneously move linearly along the guide as one body. The conveyor mechanism forms part of an applicator of the device.

Preferably the belt is sufficiently rigid to provide a supporting surface for the microneedle substrate, yet sufficiently flexible to closely follow the curvature of the rollers. Support may also be provided by providing additional rollers in the interstices between the principal rollers. Alternatively, the track may be made in rigid sections joined by a flexible linkage.

The belt may be arranged to move a fixed distance corresponding to a single delivery of drug, or it may move in small increments to deliver pre-defined quantities of drug over time, either pre-programmed, or self regulated. The conveyor mechanism may be manually operated, for example by a sliding means. Alternatively, the conveyor mechanism may be automated using a micro-mechanism to drive the conveyor along defined distances over a defined period of time to provide sustained drug release over a period of time. The mechanism for moving the conveyor along the fixed track may be a simple micro-motor, or a linear actuator such as one produced from shape memory alloy. In either case it is preferred that the pressure distribution is even over the entire body of the patch in contact with the skin.

Where the mechanism is manually operated, e.g. by hand, the device may lack the electronics for driving the microneedles over the skin, or they could be selectively switched off. The device would be housed in a suitably designed casing and driving means would be provided. A manually operated device could be used for single dose administration, e.g., the administration of vaccines. It is unlikely that the applicator would simply be rolled over the skin, and most likely will be secured to a limb using a belt/strap to ensure that when the needle is in contact with the skin the pressure is firm and even, and sustained over a period of time to ensure the drug has had time to penetrate the skin completely.

Each roller may be substantially or wholly cylindrical. Each roller, or the leading roller, may be polyhedral or have a protruding bulbous section as shown in FIG. 14. The rollers both support the belt and exert a substantially uniform pressure on the belt.

Each roller may be substantially the same size and shape to remain in contact with the belt such that the lower surface of the belt is parallel to the guide, i.e. parallel to the skin. Alternatively the rollers may be of differing sizes so that the lower side of the belt has a non planar topology for example.

The bore of each microneedle is in fluid communication with a flexible reservoir containing the drug formulation, either directly or through a solid capillary network. Each microneedle or each array of microneedles may be linked to its own reservoir, which may be isolated from other reservoirs. Each microneedle array and reservoir forms a patch.

The reservoir is preferably provided on the substrate. Preferably the reservoir is provided on the same outwardly facing surface of the substrate as the microneedles, but spaced from the microneedles parallel to the length of the belt. The reservoir is located after the microneedles on the belt relative to the direction of rotation of the belt in use. The reservoir may be a bulbous dome that projects above the microneedles when uncompressed. The reservoir may be made of a polymeric material such as methacrylates or silicone polymers for example.

The conduit connecting the reservoir to the microneedle is preferably substantially compression-resistant, and may be formed of a suitable flexible material, e.g., plastic or metal.

The conveyor frame and rollers may be composed of a dense solid material which will act to restrain the microneedles in the pierced position and depth in the skin, preventing them from detaching from the skin at the point where the drug is forced through the bore of the needle into the skin, delivering a pre-defined dose of drug.

A suitable housing may be used to cover the patch and the body of the device, which may be made of a polymeric material.

The periphery of the conveyor mechanism and patch may be adhered to the skin using a suitable adhesive, such as pharmaceutical pressure sensitive adhesives.

A belt or strap may be used to secure the device to a patient, e.g. on a limb.

The applicator may be separate from the reservoir and microneedle array or patch such that the device is re-usable, and thin films of microneedle with reservoir on a thin polymer film with adhesive backing may be supplied separately and adhered to the applicator at point of use.

The device may also be used to withdraw fluid from the skin for analysis. An example of this would be analysis of blood sugar for self-regulating insulin delivery. The device, and in particular each patch, may therefore have analytical instrumentation or microelectronics built in. To achieve the required negative pressure in the reservoir after the associated needle(s) have penetrated the skin, the reservoir may have resilient compressible channels such that when channels are compressed air is forced out through a one way valve leading to negative pressure in the chamber directly below the microneedle(s) leading to fluid withdrawal from the skin. Alternatively suction means may be applied to the patch via a port. Microneedles associated with this section of the patch may be designed to maximise fluid uptake, e.g., by making these needles slightly longer for example.

The microneedles and reservoirs may be fabricated as two separate components and then assembled into a patch, or they may be fabricated in one piece in a single process.

The microneedle component may also be made by micromoulding or embossing.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
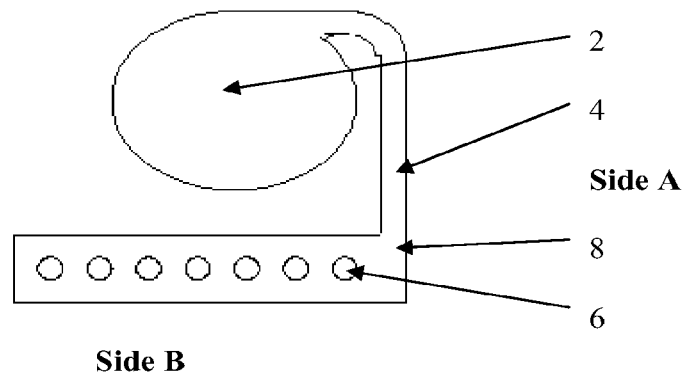
FIG. 1 is a top view of the reservoir/microneedle component.
Figure 6:
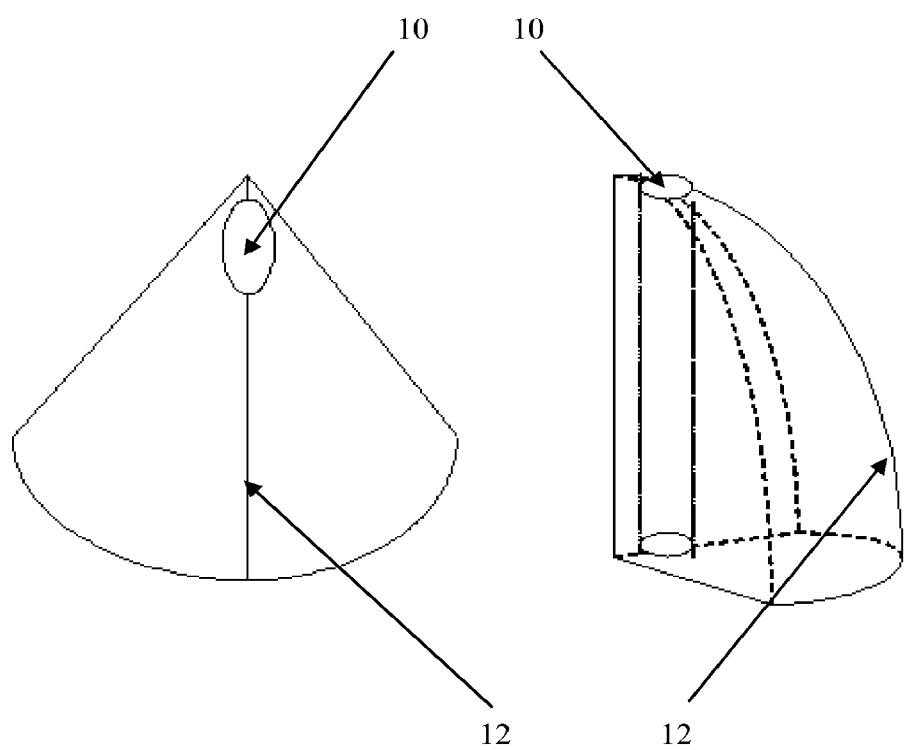
FIG. 6 is a schematic of a microneedle in top view and perspective view.
Figure 7:
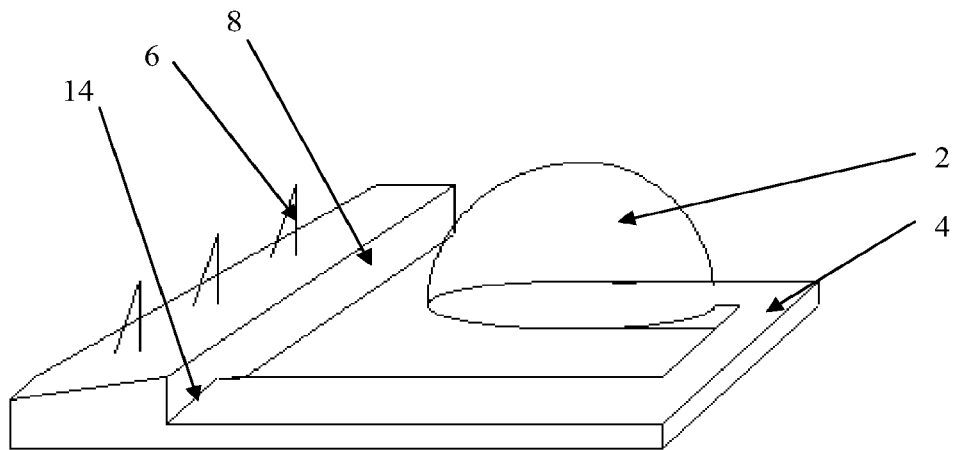
FIG. 7 is a perspective view of a reservoir/microneedle component similar to that of FIG. 1.
Figure 10:
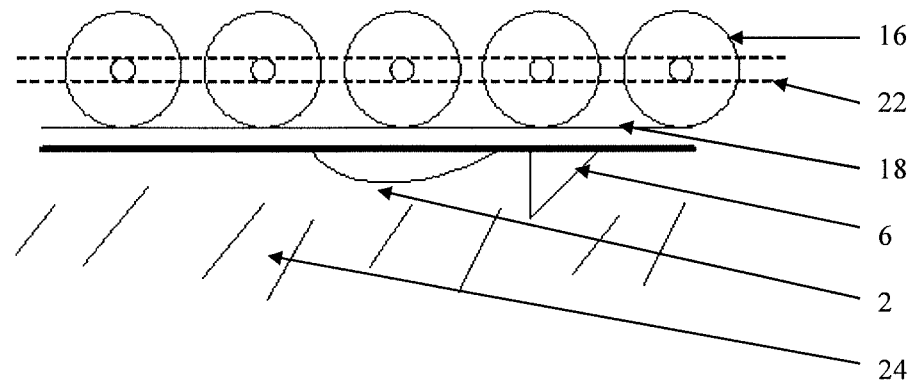
FIG. 10 is a cross section of the conveyor mechanism of FIG. 9.
Figure 11:
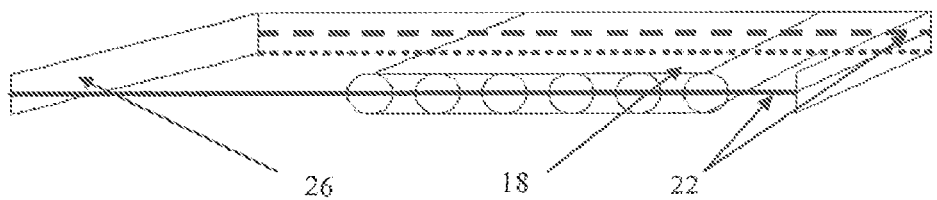
FIG. 11 is a schematic of a conveyor, support frame and glide track.

Each array of microneedles 6, as shown in FIG. 1, is mounted on a hollow, rigid chamber 8 which acts as a distribution reservoir. This is connected to a flexible polymer reservoir 2 containing a drug. When drug is forced out of the flexible reservoir 2, it will enter this chamber 8 and then be distributed to each of the needles 6, and enter the skin 24 (FIG. 10) through the bore 10 of each needle (FIG. 6). This hollow chamber 8 may be produced as an integral part at the time of fabrication of the needles 6, using a single polymer or metal substrate for both the needles 6 and chamber 8.

Design of the needle 6 will ensure the edge 12 which slices into the skin 24 is sharp and of the optimum geometry to ensure smooth penetration into the skin.

Figure 8:
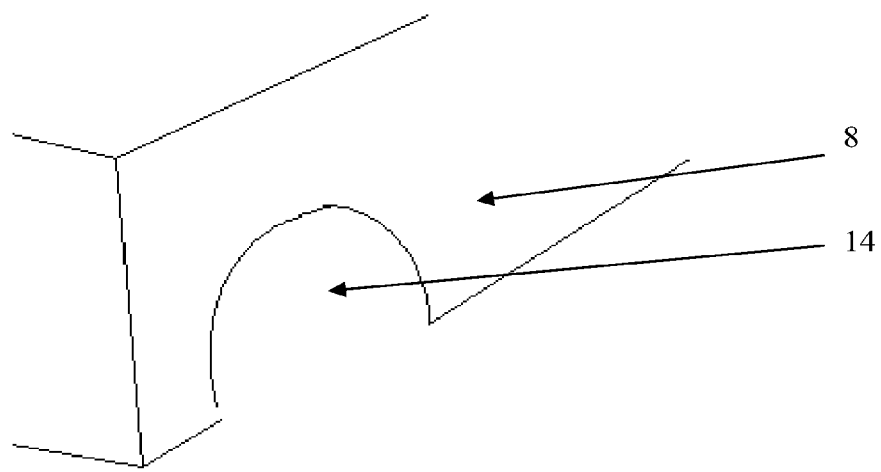
FIG. 8 is a schematic of a reservoir docking port on the microneedle chamber of FIG. 7.
Figure 9:
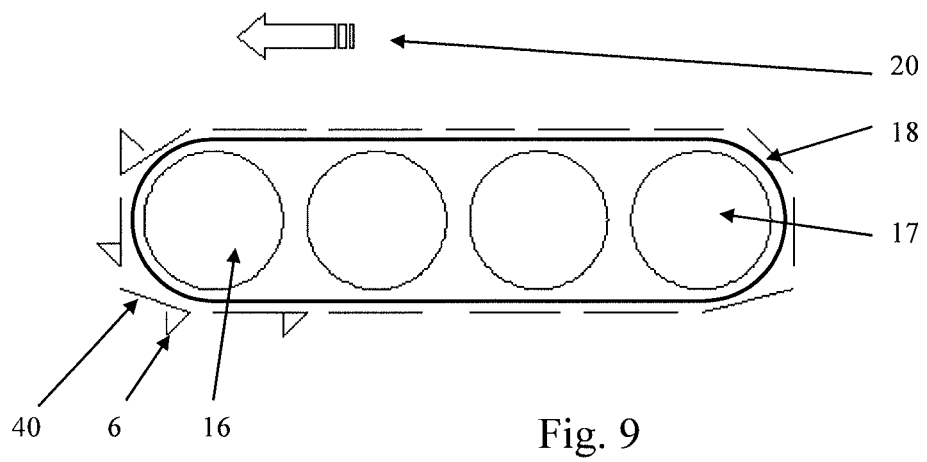
FIG. 9 is a schematic of a conveyor mechanism.

A connection port 14 (FIG. 8) provided on this chamber 8 allows the flexible reservoir 2 to be interfaced directly to this chamber 8 though a docking and locking mechanism. The docking port 14 on the flexible reservoir component may be used for the purpose of filling the reservoirs 2 with the appropriate drug formulation.

Figure 2:
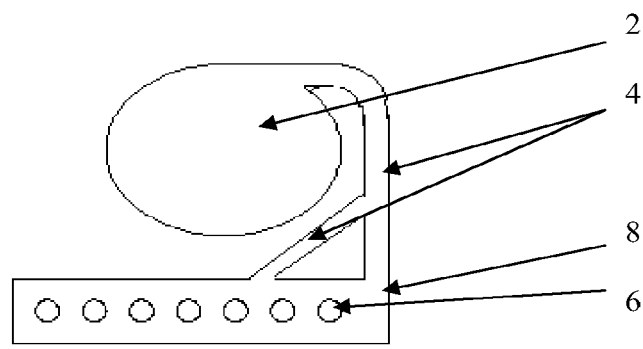
FIG. 2 is a top view of the reservoir/microneedle component with multiple channels.
Figure 3:
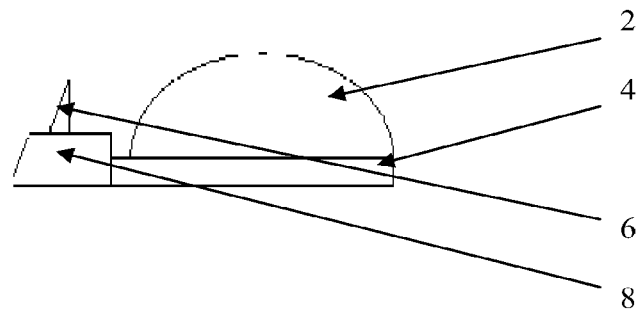
FIG. 3 is a view of the reservoir/microneedle compartment of FIG. 1 from Side A.
Figure 4:
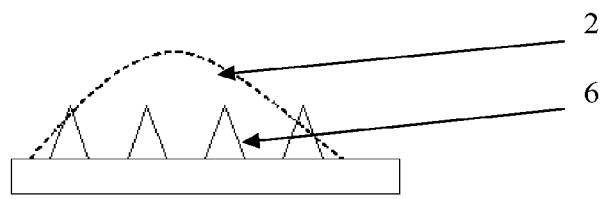
FIG. 4 is a view of the reservoir/microneedle compartment of FIG. 1 from Side B.

There may be a porous membrane or septum (not shown) between the reservoir 2 and the microneedle 6 and chamber 8 section, which will prevent drug from escaping the flexible reservoir 2 during storage but allow drug to pass through when the reservoir 2 is compressed. As can be seen in FIG. 2, there may be more than one channel 4 leading from the reservoir 2 to the microneedle chamber 8.

Figure 5:
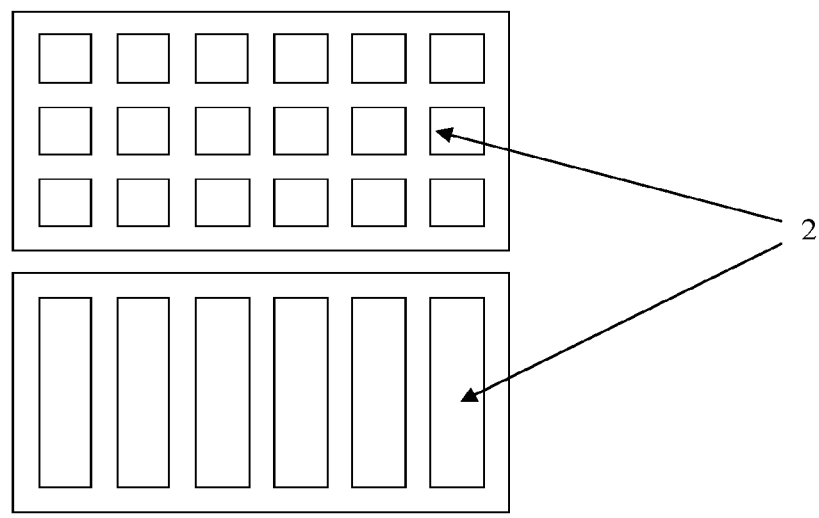
FIG. 5 is a top view of two alternative reservoir/microneedle arrays on a polymer patch.

The microneedle 6 and reservoir 2 arrays can be arranged on a thin polymer film with small, discrete reservoirs 2 or alternatively long, linear reservoirs 2, as schematically shown in FIG. 5.

The rollers 16 are mounted in a frame (not illustrated) that holds them at a fixed spacing from one another with their axes parallel, while leaving the rollers 16 free to rotate. As shown in FIGS. 9-12, the rollers 16 will be stabilised by a rigid track 22 along which they will glide, maintaining firm and even pressure across the surface of the reservoir/needle combination. The track 22 is housed in a frame 26 also composed of a rigid material. The rollers 16 are immediately interfaced to a belt 18 which may be rubber, plastic or metallic in composition. The underside of the belt 18 has teeth (not shown) which slot onto teeth (not shown) on the rollers 16 to facilitate their movement.

Figure 12:
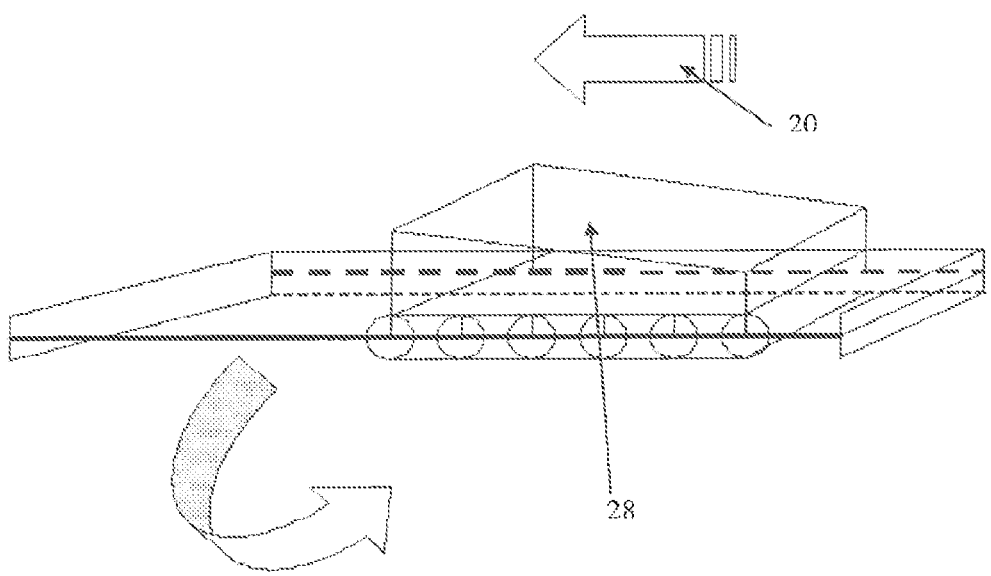
FIG. 12 is a schematic of a conveyor, support frame and glide track with manual support housing.
Figure 13:
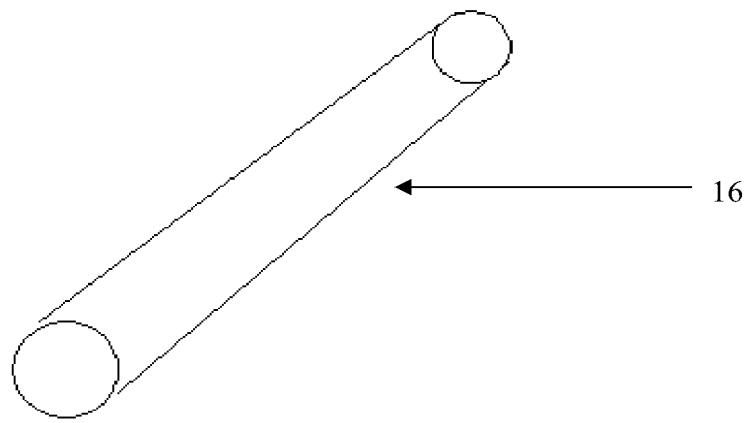
FIG. 13 is a perspective view of a roller.
Figure 14:
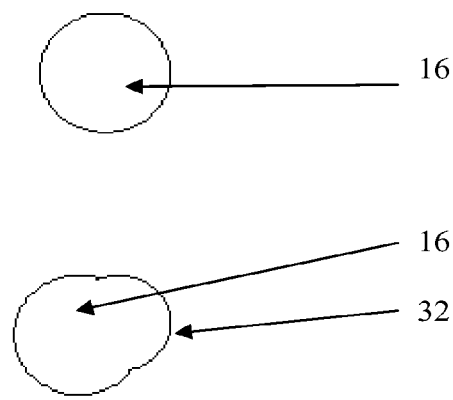
FIG. 14 is a cross section of two alternative rollers.

As shown in FIG. 14, the rollers 16 may be not completely cylindrical and may have one or more parts of the surface 32 protruding from the main body 16 of the roller to enhance the force exerted at the point at which the protruding portion 32 of the roller is directly above the reservoir 2 and/or needle 6. Alternatively, they may be mounted eccentrically about their axis of rotation. The rollers 16 may be driven either by some form of linear actuator such as shape memory wire, or a micro-mechanical system (not shown), or by hand with a suitable casing 28 to allow firm grip to be established on the device with even distribution of pressure as shown in FIG. 12.

The belt 18 has an area designated for the needle/reservoir patch 40 to be adhered. Adhesive is standard, pressure-sensitive adhesive, and one which may be easily removed when the patch 40 is removed from the applicator.

The overall dimensions of the motorised patch will be variable depending on the application. However the patch/applicator and combined electronics and actuation mechanism may be as small as a few mm in thickness.

In use, the device is attached to a suitable area of skin, for example by tightly strapping the device to a limb. Attachment for a belt or strap shall exist which may be used to secure the applicator/patch on a limb of a patient, and may be fastened using hook-and-loop fastener or an adjustable strap mechanism.

The conveyor mechanism is activated so that the conveyor moves forward along the track in the direction indicated by arrow 20 and the belt 18 rotates, so that the needles 6 are successively eased under the belt 18 and brought into contact with the skin surface 24 at which point the needles 6 gently pierce and penetrate the skin 24 as they rotate about the arc of the leading roller 16. As the conveyor continues to move forwards, the belt 18 unwraps from the first roller 16 to lie against the skin 24. The longitudinal position of the needles 6 relative to the skin 24 remains fixed, thereby avoiding tearing. As the last roller 17 in the set passes the needles 6, the belt 18 is taken up onto the last roller 16, thereby withdrawing the needles 6 from the skin 24.

The rollers 16,17 supporting the belt act to compress the reservoir 2 containing the drug against the skin 24 at a point after the microneedles 6 have penetrated the skin 24, forcing the contents of the reservoir 2 into the skin 24 via the bore 10 of the needles 6. The rollers 16, 17 may also exert pressure on a reservoir 2 and microneedle 6 simultaneously depending on the relative location of the reservoir 2 and needles 6. Alternatively the rollers 16,17 can be smaller in diameter such that a single roller is responsible for maintaining pressure on the reservoir 2 whilst another is responsible for exerting pressure on the needles 6.

Subsequent pressing of each reservoir 2 by each roller 16,17 ensures all drug is delivered.

Figure 15:
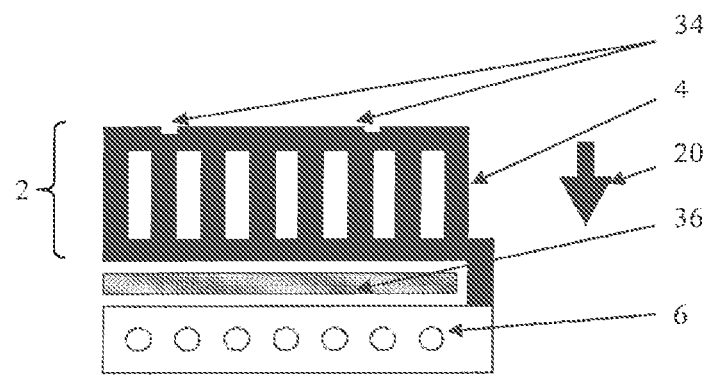
FIG. 15 is a top view of an arrangement of resilient compressible passages for sample withdrawal.
Figure 16:
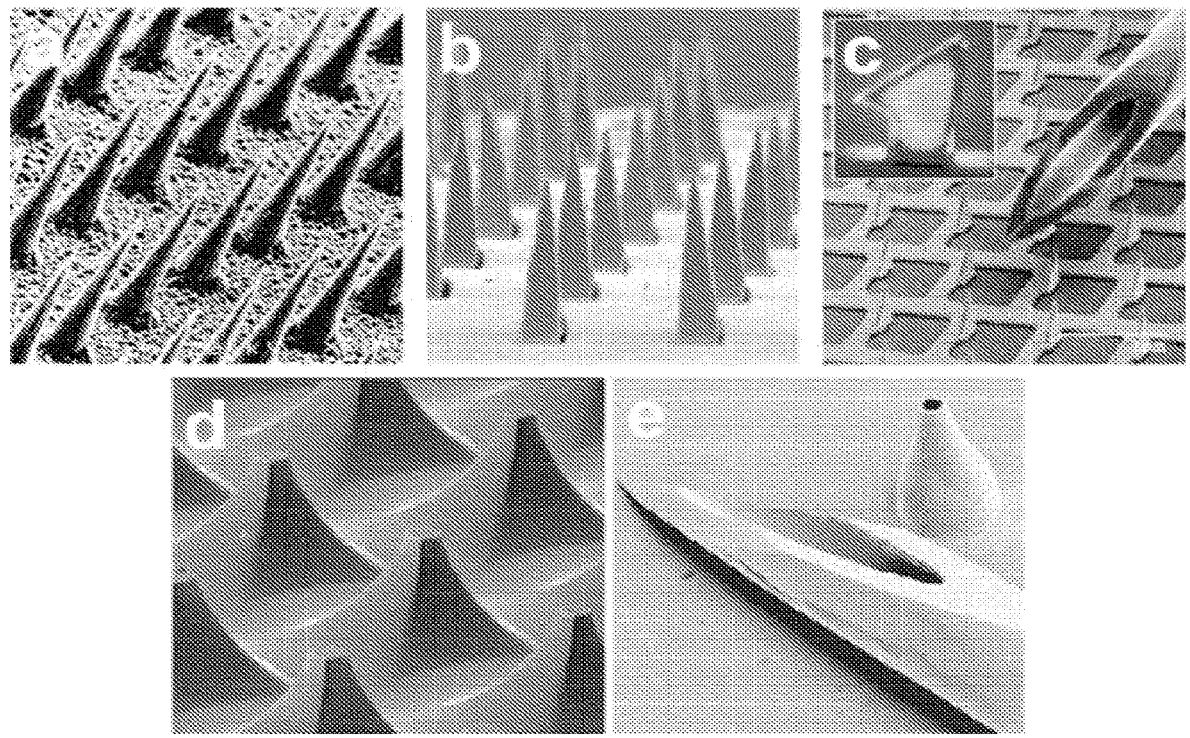
FIG. 16 is a set of photographs of known microneedles.
Figure 17:
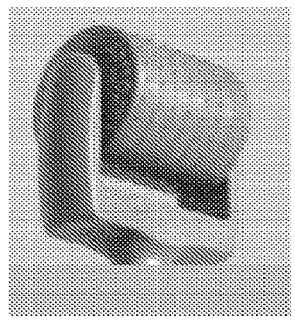
FIG. 17 is an illustration of a known Dermaroller™ device.

FIG. 15 illustrates a patch for withdrawing fluid samples from a patient for analysis, instead of delivering an agent into the patient. The patch comprises a reservoir 2 formed from flexible channels 4, which have sufficient resilience to remain normally inflated and are directly interfaced to the microneedle array 6. After the hollow needles 6 of the array have been inserted into the skin 24, the passage of the rollers 16 squeezes the channels 4 against the skin 24, thereby expelling air from the reservoir 2 through non-return valves 34 at the end of the reservoir 2 that is remote from the needles 6. As the rollers 16 move off the reservoir 2 the resilient channels 4 attempt to spring open again but air cannot enter them via the non-return valves 34. This causes a drop in pressure in the reservoir channels 4 and hence within the bores 10 of the needles 6 with which the channels 4 are interfaced, with the result that interstitial fluid or blood is withdrawn from the patient via the needles 6. A suitable sensor system 36 can be incorporated in the patch or interfaced with it to allow for in situ and real time diagnostics/measurements to be undertaken using appropriate microprocessor controls and off-the-shelf sensor components.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising" "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A transdermal device comprising:
   a reservoir of substance;
   a first roller and a second roller;
   a belt that is wrapped at least partially around the first roller and at least partially around the second roller; and
   a patch that is affixed to the belt, the patch carrying a plurality of microneedles, wherein the plurality of microneedles are fluidically coupled to the reservoir;
   wherein movement of the first roller over a skin of a patient causes the first roller to rotate and cause the plurality of microneedles to penetrate the skin of the patient under pressure from the first roller; and
   wherein the second roller is positioned to follow the first roller as it moves over the skin of the patient, to apply pressure to the belt that has unwrapped from the first roller, and to rotate and take up the belt; and
   wherein the microneedles deliver substance from the reservoir into the patient.

2. A transdermal device according to claim 1, wherein the belt is in the form of a closed loop around the first and second rollers.

3. A transdermal device according to claim 1, further comprising one or more intermediate rollers between the first and second rollers.

4. A transdermal device according to claim 3, wherein at least one of the first roller, the second roller, and the one or more intermediate rollers is asymmetrical about its axis of rotation.

5. A method of applying microneedles to a skin of a patient, the microneedles being fluidically coupled to a reservoir of substance and carried on a patch, the patch being affixed to a belt that is wrapped at least partially around a first roller and a second roller of a transdermal device, the method comprising moving the first roller and the second roller over the skin of the patient, whereby:
   as the first roller rotates, the belt unwraps from the first roller to lie against the skin, thereby causing the microneedles to penetrate the skin;
   the second roller follows the first roller over the skin of the patient, applying pressure to the belt that has unwrapped from the first roller; and as the second roller rotates, the second roller takes up the belt, thereby withdrawing the microneedles from the skin; and
   delivering substance from the reservoir through the microneedles into the patient.

6. A method according to claim 5, wherein the step of delivering substance from the reservoir comprises compressing the reservoir between the first roller and the skin to force the substance from the reservoir through the microneedles and into the patient.

7. A method of applying microneedles to a skin of a patient, the microneedles being fluidically coupled to a reservoir of substance and carried on a patch, the patch being affixed to a belt that is wrapped at least partially around a first roller and a second roller of a transdermal device, the method comprising moving the first roller and the second roller over the skin of the patient, whereby:
   as the first roller rotates, the belt unwraps from the first roller to lie against the skin, thereby causing the microneedles to penetrate the skin; and
   the second roller follows the first roller over the skin of the patient, applying pressure to the belt that has unwrapped from the first roller; and as the second roller rotates, the second roller takes up the belt, thereby withdrawing the microneedles from the skin;
   the method further comprising a step of evacuating air from the reservoir to draw fluid from the patient through the microneedles into the reservoir in response to low pressure in the reservoir.

8. A method according to claim 7, wherein the step of evacuating air from the reservoir comprises compressing the reservoir between one of the rollers and the skin to force the air out of the reservoir through a one-way valve, followed by a step of allowing the reservoir to rebound resiliently.

9. A transdermal device comprising:
   a reservoir;
   a first roller and a second roller;
   a belt that is wrapped at least partially around the first roller and at least partially around the second roller; and
   a patch that is affixed to the belt, the patch carrying a plurality of microneedles, wherein the plurality of microneedles are fluidically coupled to the reservoir;
   wherein movement of the first roller over a skin of a patient causes the first roller to rotate and cause the plurality of microneedles to penetrate the skin of the patient under pressure from the first roller; and
   wherein the second roller is positioned to follow the first roller as it moves over the skin of the patient, to apply pressure to the belt that has unwrapped from the first roller, and to rotate and take up the belt; and
   wherein the microneedles withdraw fluid from the patient into the reservoir.

10. A transdermal device according to claim 9, wherein the belt is in the form of a closed loop around the first and second rollers.

11. A transdermal device according to claim 9, further comprising one or more intermediate rollers between the first and second rollers.

12. A transdermal device according to claim 11, wherein at least one of the first roller, the second roller, and the one or more intermediate rollers is asymmetrical about its axis of rotation.

* * * * *